US008703993B2

(12) United States Patent
Hannen et al.

(10) Patent No.: US 8,703,993 B2
(45) Date of Patent: Apr. 22, 2014

(54) SYNTHESIS OF ALPHA,OMEGA-DICARBOXYLIC ACIDS AND ESTERS THEREOF FROM UNSATURATED FATTY ACID DERIVATIVES

(75) Inventors: Peter Hannen, Herten (DE); Harald Haeger, Luedinghausen (DE); Martin Roos, Haltern am See (DE)

(73) Assignee: Evonik Degussa GmbH, Essen (DE)

( * ) Notice: Subject to any disclaimer, the term of this patent is extended or adjusted under 35 U.S.C. 154(b) by 29 days.

(21) Appl. No.: 13/424,548

(22) Filed: Mar. 20, 2012

(65) Prior Publication Data
US 2012/0245375 A1    Sep. 27, 2012

(30) Foreign Application Priority Data

Mar. 25, 2011 (DE) .......................... 10 2011 015 150

(51) Int. Cl.
*C07C 69/48*      (2006.01)
(52) U.S. Cl.
USPC ......................................................... 560/190
(58) Field of Classification Search
CPC ........ C07C 51/34; C07C 55/02; C07C 55/18; C07C 67/313
See application file for complete search history.

(56) References Cited

U.S. PATENT DOCUMENTS

| 5,278,327 | A | 1/1994 | Eierdanz et al. |
| RE36,549 | E | 2/2000 | Eierdanz et al. |
| 2010/0312012 | A1 | 12/2010 | Hannen et al. |
| 2010/0324257 | A1 | 12/2010 | Karau et al. |
| 2011/0015434 | A1 | 1/2011 | Hannen et al. |
| 2012/0035393 | A1* | 2/2012 | Weber et al. .................. 562/531 |

FOREIGN PATENT DOCUMENTS

| DE | 37 15 464 A1 | 11/1988 |
| GB | 841653 | 7/1960 |
| SU | 330154 A1 * | 12/1972 |
| WO | WO 2011/110249 A1 | 9/2011 |

OTHER PUBLICATIONS

U.S. Appl. No. 13/806,555, filed Dec. 21, 2012, Hannen, et al.
U.S. Appl. No. 13/634,111, filed Sep. 11, 2012, Petrat, et al.
European Search Report issued Aug. 22, 2012, in European Patent Application No. 12159467.5.

* cited by examiner

*Primary Examiner* — Paul A Zucker
(74) *Attorney, Agent, or Firm* — Oblon, Spivak, McClelland, Maier & Neustadt, L.L.P.

(57) ABSTRACT

A process for preparing an alpha, omega-dicarboxylic acid or an ester thereof, which includes (a) subjecting at least one unsaturated fatty acid or fatty acid derivative to ozonolysis to obtain an ozonolysis reaction mixture; and (b) oxidizing the ozonolysis reaction mixture with an oxidizing agent in the presence of an acid catalyst to obtain an oxidized reaction mixture comprising at least one alpha, omega-dicarboxylic acid or ester; wherein the process is performed using a solvent and the acid catalyst has a pKa of less than or equal to zero, as measured at 25° C.

14 Claims, No Drawings

SYNTHESIS OF ALPHA,OMEGA-DICARBOXYLIC ACIDS AND ESTERS THEREOF FROM UNSATURATED FATTY ACID DERIVATIVES

CROSS REFERENCE TO RELATED APPLICATIONS

This application claims priority to German Application No. 102011015150.8, filed Mar. 25, 2011, the disclosure of which is incorporated herein by reference in its entirety.

BACKGROUND OF THE INVENTION

1. Field of the Invention

The invention relates to a process for preparing alpha, omega-dicarboxylic acids or esters thereof by ozonolysis and subsequent oxidation.

2. Description of the Related Art

Ozonolysis in the context of the invention is understood to mean the cleavage of a carbon-carbon double bond by the action of ozone. According to the mode of workup, carbonyl compounds, alcohols or carboxylic acids may be obtained.

alpha,omega-Dicarboxylic acids are understood to mean carboxylic acids with two carboxyl groups, the carbon chain being substituted by a carboxyl group at position 1 and at the terminal position.

The ozonolysis of olefins is an important method for preparation of carboxylic acids, aldehydes and alcohols (Baily, P. S., Ozonation in Organic Chemistry, Academic: New York, N.Y., 1978, Vol. 1.). At the core of this reaction type is the 1,3-dipolar cycloaddition of ozone onto a C,C-double bond of an olefin (1) to form the primary ozonide (1,2,3-trioxolane, 2). This species is an unstable intermediate which decomposes directly to an aldehyde fragment (3) and a carbonyl oxide (4) (scheme 1).

Chemistry); Kropf H. ed.; Georg Thieme: Stuttgart, 1988; Vol. E13/2, p. 1111.; Smith, M. B., March, J. March's Advanced Organic Chemistry; John Wiley & Sons, Inc; 2001, 5th ed., p. 1522). The aldehydes in turn can be reduced further to the alcohol.

A significant disadvantage of this reaction sequence is the formation of the usually explosive secondary ozonides, polymeric peroxides or 1,2,4,5-tetraoxolanes, some of which are stable compounds and can thus accumulate in downstream reaction and workup steps and constitute a considerable risk (Kula, J. Chem. Health Saf. 1999, 6, 21; Gordon, P. M. Chem. Eng. News 1990, 68, 2). Furthermore, in the case of an oxidative or reductive workup of secondary ozonides, one oxidation or reduction equivalent must be used (oxygen, hydrogen peroxide, or dimethyl sulphide, triphenylphosphine, etc.).

A further problem occurs in the oxidation reaction. If the oxidation is performed at relatively low temperatures, it proceeds very slowly, but an increase in the temperature leads to increased formation of by-products which have to be removed in a complex manner in further process steps. One example of such further processing is chain degradation by decarboxylation.

SUMMARY OF THE INVENTION

The technical object addressed by the present invention is therefore that of providing an improved process for preparing alpha,omega-dicarboxylic acids or esters thereof, which avoids the formation of ozonides and enables a direct conversion of the reaction product from the ozonolysis for the oxidation.

A further technical object addressed is that of modifying the process such that the oxidation of the reaction mixtures obtained from the ozonolysis may be accelerated.

Scheme 1: Mechanism of ozonolysis with subsequent workup.

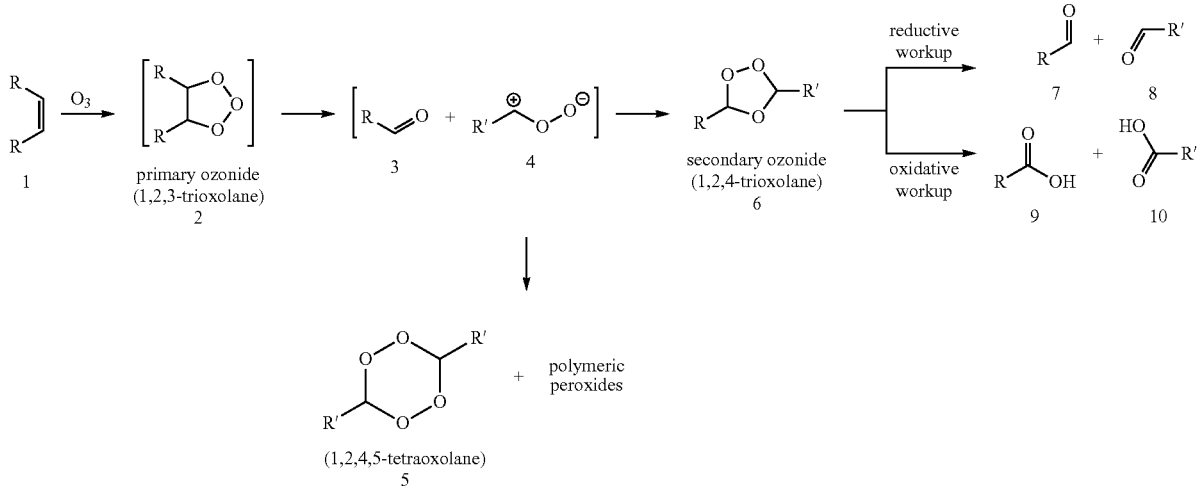

The carbonyl oxide can firstly polymerize or dimerize to give a 1,2,4,5-tetraoxolane (5), or recombine in a further cycloaddition to give a secondary ozonide (1,2,4-trioxolane, 6). Proceeding from compound 6, it is possible to prepare aldehydes (7, 8) via a reductive workup, or carboxylic acids (9, 10) via an oxidative workup (Kropf, H., Houben-Weyl Methoden Der Organischen Chemie (Methods of Organic These and other objects have been achieved by the present invention, the first embodiment of which includes a process for preparing an alpha, omega-dicarboxylic acid or an ester thereof, the process comprising:

a. subjecting at least one unsaturated fatty acid or fatty acid derivative to ozonolysis to obtain an ozonolysis reaction mixture;

b. oxidizing the ozonolysis reaction mixture with an oxidizing agent to obtain an oxidized reaction mixture comprising at least one alpha, omega-dicarboxylic acid or ester thereof;

wherein a strong acid catalyst with a pKa of less than or equal to zero, measured at 25° C., is added to the oxidation (b) and the process is conducted in a solvent.

In a preferred embodiment of the present invention the acid catalyst is at least one selected from the group consisting of sulphuric acid, hydrochloric acid, nitric acid and perchloric acid.

In a highly preferred embodiment the ozonolysis (a) and the oxidation (b) are conducted in direct succession without isolating or working up the reaction mixture from the ozonolysis.

DETAILED DESCRIPTION OF THE PREFERRED EMBODIMENTS

In a first embodiment, the present invention provides a process for preparing an alpha, omega-dicarboxylic acid or an ester thereof, the process comprising:

a. subjecting at least one unsaturated fatty acid or fatty acid derivative to ozonolysis to obtain an ozonolysis reaction mixture;

b. oxidizing the ozonolysis reaction mixture with an oxidizing agent to obtain an oxidized reaction mixture comprising at least one alpha, omega-dicarboxylic acid or ester thereof;

wherein a strong acid catalyst with a pKa of less than or equal to zero, measured at 25° C., is added to the oxidation (b) and the process is conducted in a solvent.

It has been found that, surprisingly, alpha,omega-dicarboxylic acids or esters thereof may be formed easily in one step via an ozonolysis and subsequent oxidation. It may be essential that the dicarboxylic acids are formed via aldehydes formed as intermediates and not via the oxidation of secondary ozonides.

In the process according to the invention, no polymeric or oligomeric ozonides are obtained in the ozonolysis step. An important aspect of the invention described may be the distinct acceleration of the oxidation as a result of the addition of catalytic amounts of a strong acid.

The process according to the invention should be regarded as a combination of ozonolysis and oxidation. The reaction mixture from the ozonolysis may be subjected without workup to the conditions for a further oxidation to the dicarboxylic acid derivative.

In a preferred embodiment, the catalyst may be an acid selected from the group consisting of sulphuric acid, hydrochloric acid, nitric acid, perchloric acid and mixtures thereof. The use of concentrated sulphuric acid or perchloric acid may be particularly preferred.

In the reaction, it may be possible to use various solvents. For instance, it is known that a solution of 5 to 10% by weight of water in acetone allows selective preparation of nonanal and methyl 9-oxononanoate from methyl oleate via an ozonolysis (Dussault, P. H., Journal of Chemistry 2008, 73, 4688-4690).

In the preparation process according to the present invention, it may be possible to use other solvents than acetone, for example, methyl ethyl ketone, alcohols (such as isopropanol, tert-butanol, etc.) or carboxylic acids with comparably good results.

In a preferred embodiment, the solvent may be an aliphatic carboxylic acid in a mixture with at least 0.5% by weight of water, based on the total amount of solvent.

In a particularly preferred embodiment, the solvent may contain 1 to 20% by weight of water. This amount includes all values and subvalues therebetween including most preferably 2 to 15% by weight of water, based on the total amount of solvent.

In a particularly preferred embodiment, the proportion of water in the reaction mixture may be at least in a stoichiometric amount relative to the number of converted double bonds of the fatty acid or the fatty acid derivative.

The solvent may preferably be a $C_1$-$C_{15}$ aliphatic carboxylic acid, more preferably a $C_3$-$C_{10}$ aliphatic carboxylic acid. Very particular preference may be given to propionic acid, acetic acid or a mixture of propionic acid and acetic acid.

The fatty acids or esters thereof having at least one double bond employed as starting materials in the present invention may preferably be unsaturated fatty acids or fatty acid derivatives, which may be selected from the group consisting of oleic acid, oleic acid alkyl esters, undecylenoic acid, undecylenoic acid alkyl esters, erucic acid, erucic acid alkyl esters and mixtures thereof.

In a preferred embodiment, the oxidation (b) may be conducted at a temperature of less than or equal to 110° C., more preferably of less than or equal to 100° C. The process may be performed continuously or batchwise.

The oxidizing agent according to the present invention may preferably be hydrogen peroxide, a peroxocarboxylic acid or a mixture of hydrogen peroxide and a peroxocarboxylic acid. One equivalent of hydrogen peroxide per double bond cleaved forms in the ozonolysis through the action of the water with the primary ozonide, and may be used with particular preference in the oxidation step. Peroxocarboxylic acids are likewise preferred because they can form from the hydrogen peroxide together with the carboxylic acids present as solvents.

The process may be notable for its safe performance compared to conventionally known processes. Ozonides, or the carbonyl oxide formed as an intermediate, are scavenged directly by water. The adduct of ozonide and water, referred to as hydroperoxide 11, is present in equilibrium with aldehyde 12 and hydrogen peroxide (scheme 2).

Scheme 2: Scavenging of the carbonyl oxide 4 with water and subsequent reversible elimination of hydrogen peroxide

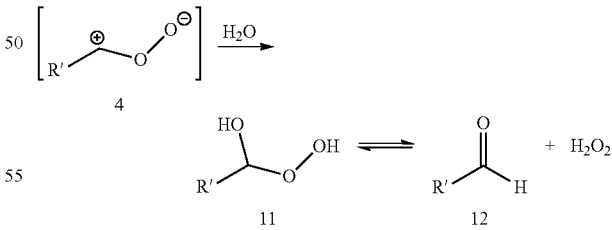

The formation of hydrogen peroxide in the ozonolysis may be utilized particularly advantageously in an oxidative workup. In addition to the avoidance of formation of hazardous ozonides, which has already been mentioned, the reaction directly forms one oxidation equivalent.

The equilibrium shown in scheme 2 may be used with establishment of suitable reaction conditions to oxidize a carbonyl group to the carboxyl group. As shown in scheme 3, hydrogen peroxide may first add reversibly onto aldehyde 3 to form hydroperoxide 13. With elimination of a hydrogenium ion, the carboxyl compound 9 is formed irreversibly from adduct 13. This reaction proceeds preferably at relatively high temperatures of 100 to 200° C., preferably of 150° C.

Scheme 3: Addition of hydrogen peroxide with subsequent decomposition of the hydroperoxide to the carboxylic acid

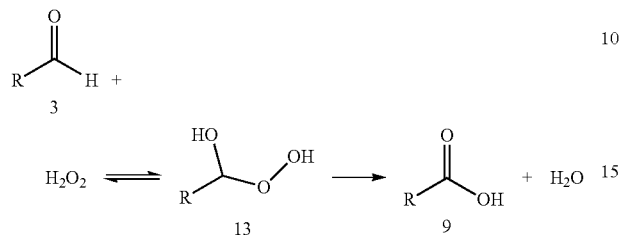

The oxidation at temperatures below 100° C. proceeds comparatively slowly without catalysts, and an increase in the temperature may not be an option due to the increased formation of by-products.

It has been surprisingly found that addition of catalytic amounts of an acid may greatly accelerate the decomposition of the hydroperoxide and hence the oxidation overall. Firstly, it may thus be possible to significantly shorten the reaction time; secondly, this may be combined with the possibility of reaction at much lower temperatures. The formation of unwanted by-products as a result of a long reaction time at high temperature may thus be avoided. Although not being restricted by mechanism, it may be assumed that the protonation of the hydroperoxide group favours the decomposition (scheme 4).

Scheme 4: Accelerated decomposition of the hydroperoxide to the carboxylic acid by acid catalysis

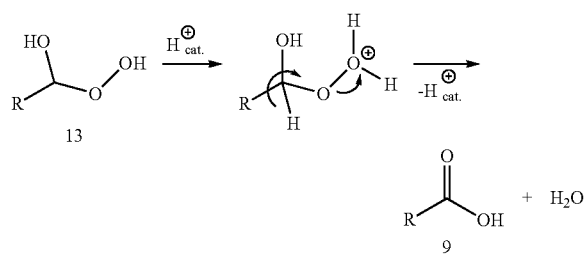

A distinct catalytic effect in the reaction described may, however, be exhibited only by acids having a $pK_a$ of less than or equal to 0, as measured at 25° C.

For example, the reaction may be greatly accelerated by catalytic amounts of conc. sulphuric acid or perchloric acid. Particular preference may be given to the use of sulphuric acid as a catalyst.

As well as the direct reaction of the carbonyl group with hydrogen peroxide to give the carboxyl group shown in scheme 4, oxidation by a peroxocarboxylic acid may also be conceivable under the reaction conditions. The peroxocarboxylic acid forms under acid catalysis from the carboxylic acid used as a solvent and hydrogen peroxide. The peroxocarboxylic acid may add on to the carbonyl group and then decompose to form two carboxyl groups.

In order to oxidize both fragments from the ozonolysis (scheme 1, compounds 3 and 4) to the corresponding carboxylic acid, a further oxidation equivalent may be required. In the process according to the invention, this may be achieved in a particularly simple manner by the addition of a further equivalent of hydrogen peroxide, which results in full oxidation to the carboxylic acids (scheme 5).

Scheme 5: Ozonolysis with subsequent oxidation by additions of hydrogen peroxide

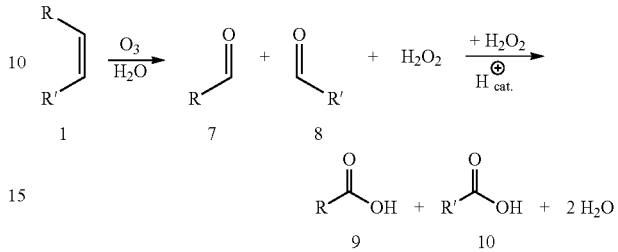

The use of hydrogen peroxide as an oxidizing agent additionally has the advantage that it has good meterability and, after the reaction, only water forms as a decomposition product. These may be crucial advantages for an industrial process over, for example, the use of atmospheric oxygen as an oxidizing agent, since the reaction system is in monophasic form and cannot form any explosive gas mixtures, and there is no need for any complex removal of entrained reaction mixture in the offgas stream. The oxidation may be performed batchwise or continuously. In a continuous oxidation, preference may be given to use of a capillary reactor in which there is good heat exchange.

A further advantage of the acid-catalysed oxidation may be in the simultaneous cleavage of the ester group in the case of use of appropriate fatty acid esters. As a result, one of the products is not present as the dicarboxylic monoester, bur rather as the dicarboxylic acid, which may distinctly simplify workup of the reaction mixture.

The fatty acids or fatty acid derivatives to be treated according to the present invention have at least one double bond. The fatty acids and fatty acid derivatives are especially preferably compounds selected from the group consisting of oleic acid, oleic acid alkyl esters, undecylenoic acid, undecylenoic acid alkyl esters, erucic acid, erucic alkyl esters and mixtures thereof.

However, the starting materials for the process according to the invention may also be other unsaturated fatty acids or fatty acid derivatives. Examples of these may include myristoleic acid, palmitoleic acid, petroselic acid, elaidic acid, vaccenic acid, gadoleic acid, eicosenoic acid, cetoleic acid and nervonic acid, and esters thereof. These are monounsaturated fatty, acids. In addition, it is also possible to use polyunsaturated fatty acids, including, for example, linoleic acid, linolenic acid, calendulic acid, punicic acid, elaeostearic acid, arachidonic acid, timnodonic acid, clupanodonic acid and cervonic acid, or esters thereof.

The process according to the invention may be conducted as follows. The ozonolysis may first be performed in a solvent, which may preferably be a carboxylic acid. Carboxylic acids particularly suitable as solvents may include propionic acid, acetic acid or pelargonic acid. The unsaturated fatty acid ester may be present in a concentration of 0.1 to 1 mol/l. At such relatively high concentrations of fatty acid esters, it may be ensured that the amount of water added is always at least stoichiometric relative to the number of double bonds converted. The reaction mixture may preferably be in monophasic form. In principle, the reaction may also be conducted in a polyphasic reaction mixture. The ozonolysis may be performed preferably within the temperature range from 0 to 50° C., particular preference being given to a reaction temperature from 20 to 30° C.

Ozonolysis in the context of the present invention is understood to mean the reaction of a fatty acid or of a fatty acid derivative with ozone.

Typically, an ozone generator may be used for ozone production. This ozone generator may use compressed air or a mixture of carbon dioxide and oxygen as the feed gas. In the ozone generator, the ozone is produced by stationary electric discharge. This forms reactive oxygen species which react with oxygen molecules to give ozone.

The reaction mixture obtained from the ozonolysis may be subjected to the oxidation step without further workup and removal. For this purpose, an oxidizing agent may be used, which is preferably hydrogen peroxide or a peroxycarboxylic acid. Based on the number of double bonds in the substrate (fatty acid or fatty acid derivative), a further equivalent of oxidizing agent may be added and the mixture heated to temperatures in the region of less than or equal to 110° C., preferably less than or equal to 100° C. Very particular preference may be given to performing the reaction within a temperature range from 90 to 110° C. The oxidation may also be performed at lower temperatures, although the reaction may proceed more slowly. At reaction temperatures above 110° C., the formation of the reaction products may be accelerated, but a higher concentration of by-products may also be obtained.

The reaction sequence of ozonolysis and oxidation may be conducted continuously, in which case the ozonolysis preferably may take place in a trickle bed reactor in which the reactants are conducted in countercurrent over a packed bed. Directly connected to the ozonolysis section is a capillary reactor, in which the oxidation is effected. Between the ozonolysis and oxidation sections of the apparatus, the oxidizing agent, preferably hydrogen peroxide, may be metered continuously into the reaction mixture.

The process according to the invention may provide the following advantages:

Secondary and oligomeric ozonides are avoided through the addition of water. This makes the process according to the invention safer since these substances are explosive.

A further advantage may be that, in the process according to the invention, in addition to formation of one equivalent each of the two possible aldehyde intermediates, one equivalent of hydrogen peroxide is formed, which can be used for the oxidation in the further reaction.

A further advantage may be that the oxidation proceeds to completion, and the aldehydes formed as an intermediate react through addition of only one additional equivalent of hydrogen peroxide to give the corresponding carboxylic acids, while the other equivalent results from the reaction in the ozonolysis.

In addition, the reaction is accelerated by catalytic addition of a strong acid and may thus be performed more economically.

Having generally described this invention, a further understanding can be obtained by reference to certain specific examples which are provided herein for purposes of illustration only, and are not intended to be limiting unless otherwise specified.

EXAMPLES

Example 1

Comparative Example

Ozonolysis and Oxidation without Addition of Acid 20 g of a 0.182 molal solution of methyl oleate (95% pure) in a solvent mixture of propionic acid and water (15 equivalents based on moles of double bond) were initially charged in a two-neck flask with gas inlet tube and reflux condenser. The feed gas, consisting of 5% by volume of oxygen in carbon dioxide was passed through an ozone generator at a flow rate of 40 ml/min. The ozone generator was set to maximum power. The ozone-containing gas mixture was passed into the reaction mixture with stirring. The offgas stream was passed by means of gas wash bottles into a 5% aqueous potassium iodide solution. After 60 minutes, the substrate was converted, and the gas introduction was then stopped. According to GC analysis, the reaction mixture had a content of 39.5 wt % of 9-nonanal and 38.2 wt % of methyl 9-oxononanoate.

After adding hydrogen peroxide (0.454 g of a 30% aqueous solution), the reaction mixture was then heated to 100° C. in an oil bath. After 120 minutes, nonanal and methyl 9-oxononanoate were converted completely to the respective carboxyl compounds. GC analysis: 41.05% pelargonic acid, 39.65% monomethyl azelate (FID signal, figure in area percent, uncorrected).

Example 2

Ozonolysis and Oxidation with Addition of Acid 20 g of a 0.182 molal solution of methyl oleate (95% pure) in a solvent mixture of propionic acid and water (15 equivalents based on moles of double bond) were initially charged in a two-neck flask with gas inlet tube and reflux condenser. The feed gas, consisting of 5% by volume of oxygen in carbon dioxide was passed through an ozone generator at a flow rate of 40 ml/min. The ozone generator was set to maximum power. The ozone-containing gas mixture was passed into the reaction mixture with stirring. The offgas stream was passed by means of gas wash bottles into a 5% aqueous potassium iodide solution. After 60 minutes, the substrate was converted, and the gas introduction was then stopped. According to GC analysis, the reaction mixture has a content of 39.5% of 9-nonanal and 38.2% of methyl 9-oxononanoate.

After adding hydrogen peroxide (0.454 g of a 30% aqueous solution) and sulphuric acid (0.019 g, 95%) the reaction mixture was then heated to 100° C. in an oil bath. After 75 minutes, nonanal and methyl 9-oxononanoate were converted completely to the respective carboxyl compounds. GC analysis: 40.22% pelargonic acid, 38.50% azelaic acid derivative (21.90% monomethyl azelate+16.6% azelaic acid) (FID signal, figure in area percent, uncorrected).

The invention claimed is:

1. A process for preparing an alpha, omega-dicarboxylic acid or an ester thereof, the process comprising:
   (a) preparing a solution of at least one unsaturated fatty acid or fatty acid derivative in an aliphatic carboxylic acid and water mixture wherein the content of water is at least a stoichiometric amount of water relative to the number of double bonds of the fatty acid or fatty acid derivative to be oxidized;
   (b) subjecting the unsaturated fatty acid or fatty acid derivative solution to ozonolysis to obtain an ozonolysis reaction mixture;
   (c) adding a catalytic amount of an acid having a pKa of less than or equal to zero, measured at 25° C., to the ozonolysis reaction mixture following completion of the ozonolysis without workup; and
   (d) oxidizing the ozonolysis reaction mixture with an oxidizing agent to obtain an oxidized reaction mixture comprising at least one alpha, omega-dicarboxylic acid or ester thereof;
   wherein
   the acid with a pKa of less than or equal to zero, measured at 25° C., comprises at least one selected from the group consisting of sulphuric acid, hydrochloric acid, nitric acid and perchloric acid.

2. The process according to claim 1, wherein the content of water is from 5 to 10% by weight, based on the total amount of solvent.

3. The process according to claim 1, wherein the at least one unsaturated fatty acid or fatty acid derivative comprises at least one double bond.

4. The process according to claim 1, wherein the ozonolysis (a) and the oxidation (b) are conducted in direct succession without isolating or working up the reaction mixture from the ozonolysis.

5. The process according to claim 1, wherein the at least one unsaturated fatty acid or fatty acid derivative is selected from the group consisting of oleic acid, an oleic acid alkyl ester, undecylenoic acid, an undecylenoic acid alkyl esters, erucic acid, and an erucic acid alkyl ester.

6. The process according to claim 1, wherein the aliphatic carboxylic acid is a $C_1$ to $C_{15}$ aliphatic carboxylic acid.

7. The process according to claim 1, wherein the aliphatic carboxylic acid is propionic acid, acetic acid or a mixture of propionic acid and acetic acid.

8. The process according to claim 1, wherein a temperature of the oxidation (b) is less than or equal to 110° C.

9. The process according to claim 1, wherein the process is conducted continuously or batchwise.

10. The process according to claim 1, wherein the oxidizing agent is at least one of hydrogen peroxide and a peroxocarboxylic acid.

11. The process according to claim 6, wherein the aliphatic carboxylic acid is a $C_3$ to $C_{10}$ aliphatic carboxylic acid.

12. The process according to claim 8, wherein the temperature is less than or equal to 100° C.

13. The process according to claim 4, comprising formation of an aldehyde in the ozonolysis and oxidation of the aldehyde to the alpha, omega-dicarboxylic acid or ester.

14. The process according to claim 9, wherein the process is continuous and the oxidation of the ozonolysis reaction mixture is conducted in a capillary reactor.

* * * * *